US009404860B2

(12) United States Patent
Agashe et al.

(10) Patent No.: US 9,404,860 B2
(45) Date of Patent: Aug. 2, 2016

(54) MICRO-ELECTRO-MECHANICAL SYSTEM OPTICAL SENSOR WITH TILT PLATES

(71) Applicant: Apple Inc., Cupertino, CA (US)

(72) Inventors: Janhavi S. Agashe, Santa Clara, CA (US); Jae H. Lee, Palo Alto, CA (US)

(73) Assignee: Apple Inc., Cupertino, CA (US)

( * ) Notice: Subject to any disclaimer, the term of this patent is extended or adjusted under 35 U.S.C. 154(b) by 127 days.

(21) Appl. No.: 14/330,723

(22) Filed: Jul. 14, 2014

(65) Prior Publication Data

US 2015/0323456 A1 Nov. 12, 2015

Related U.S. Application Data

(60) Provisional application No. 61/991,067, filed on May 9, 2014.

(51) Int. Cl.
*G01N 21/55* (2014.01)
*G01N 21/01* (2006.01)
*B81C 1/00* (2006.01)

(52) U.S. Cl.
CPC ............ *G01N 21/55* (2013.01); *B81C 1/00341* (2013.01); *G01N 21/01* (2013.01); *B81C 1/00158* (2013.01); *B81C 2201/0174* (2013.01); *G01N 2201/0612* (2013.01); *Y10T 29/413* (2015.01)

(58) Field of Classification Search
CPC .............................. G01N 21/01; G01N 21/55
USPC ......................................................... 356/445
See application file for complete search history.

(56) References Cited

U.S. PATENT DOCUMENTS

| | | | |
|---|---|---|---|
| 7,826,629 B2 * | 11/2010 | Miles | H04R 23/006 250/237 G |
| 8,205,497 B1 | 6/2012 | Okandan et al. | |
| 8,391,527 B2 | 3/2013 | Avenson et al. | |
| 8,503,701 B2 * | 8/2013 | Miles | H04R 23/006 356/498 |
| 8,928,967 B2 * | 1/2015 | Miles | G02B 26/0841 359/291 |
| 9,110,289 B2 * | 8/2015 | Miles | G02B 26/001 |
| 2005/0105098 A1 | 5/2005 | Johansen et al. | |
| 2016/0007108 A1 * | 1/2016 | Lee | H04R 1/08 381/111 |

OTHER PUBLICATIONS

Cui, Weili, et al., "Optical Sensing in a Directional MEMS Microphone Inspired by the Ears of the Parasitoid Fly, *Ormia ochracea*", IEEE MEMS 2006, Istanbul, Turkey, (Jan. 22-26, 2006), 614-617.
Peach, Matthew, "Optical microphone offers greater sensitivity", Retrieved from optics.org on Feb. 17, 2014, (Jul. 4, 2013), 2 pages.
Williamson Labs, "Laser Microphone", Retrieved from williamson-labs.com on Feb. 27, 2014, 8 pages.

* cited by examiner

*Primary Examiner* — Roy M Punnoose
(74) *Attorney, Agent, or Firm* — Blakely, Sokoloff, Taylor & Zafman LLP (57) ABSTRACT

A micro-electro-mechanical system (MEMS) optical sensor, method of detecting sound using the MEMS optical sensor and method of manufacturing. The MEMS optical sensor including a substrate having a base portion and a vertically extending support portion. The sensor further including a top plate having a compliant membrane configured to vibrate in response to acoustic waves, the top plate connected to the support portion and having a reflective surface. The sensor also includes a back plate connected to the support portion, the back plate having a grating portion positioned below the reflective surface portion and a base plate connected to the support portion at a position below the back plate. A light emitter, a light detector and circuitry operable to tilt the top plate and the back plate with respect to the base plate so as to direct the reflected laser light toward the light detector are further provided.

11 Claims, 10 Drawing Sheets

MICRO-ELECTRO-MECHANICAL SYSTEM OPTICAL SENSOR WITH TILT PLATES

CROSS-REFERENCE TO RELATED APPLICATIONS

The application claims the benefit of the earlier filing date of co-pending U.S. Provisional Patent Application No. 61/991,067, filed May 9, 2014 and incorporated herein by reference.

FIELD

An embodiment of the invention is directed to a micro-electro-mechanical system (MEMS) device having a tilted plate, more specifically, a MEMS optical microphone having a tilted compliant membrane and back plate. Other embodiments are also described and claimed.

BACKGROUND

MEMS devices generally range in size from about 20 micrometers to about 1 millimeter and are made up of a number of even smaller components which can be formed in layers on a substrate using various MEMS processing techniques (e.g. deposition processes, patterning, lithography, etching, etc.). MEMS devices can be processed for many different applications, for example, they may be sensors or actuators. One such type of MEMS sensor is a laser microphone. A MEMS laser, or optical, microphone refers to a microphone which uses a laser beam to detect sound vibrations of an associated diaphragm. The microphone may include two essentially flat, horizontally arranged, surfaces. One of the surfaces may be a diaphragm, which can vibrate in response to sound waves, and the other surface may be a substantially stiff structure having a grating. A light emitter and a light detector may be associated with a substrate positioned below the flat surfaces. The light emitter may be a laser (e.g. a vertical cavity surface emitting laser (VCSEL)) configured to direct a light beam toward a reflective portion of the diaphragm. The light beam is diffracted by the grating and reflected off of the reflective portion back to the light detector. The light detector detects the interference pattern created by the diffracted light rays and converts the light into an electrical signal, which corresponds to an acoustic vibration of the diaphragm, which in turn provides an indication of sound.

SUMMARY

An embodiment of the invention is directed to a MEMS sensor such as a very high SNR (signal-to-noise ratio) laser (or optical) MEMS microphone having one or more layers, plates or membranes which can be tilted to modify an alignment between a light source (which is stationary) and a reflective layer (e.g. a diaphragm having a reflective portion). For proper operation of an optical microphone, the light beam from the light source should be properly aligned with a reflective portion of the diaphragm. Proper alignment, however, can be difficult in MEMS type structures in which it is not feasible to mass manufacture tilted surfaces and layers. The MEMS sensor can be formed by MEMS processing techniques suitable for forming one or more plates (e.g. electrodes) which can be tilted.

An embodiment of the invention solves the alignment problem in an optical microphone by allowing for the manufacture of a MEMS structure, for example, an optical MEMS microphone, having a compliant membrane (e.g. diaphragm) with a reflective surface and a back plate having a grating, both of which can be tilted, with respect to a light source, by applying a voltage. Representatively, the compliant membrane may be formed over a substrate and may have a reflective surface portion. The compliant membrane may have a first end movably connected to a vertically extending portion of the substrate, and a second, free end. The back plate may be positioned below, and substantially parallel to, the compliant membrane and may include a grating portion. The back plate may have a first end movably connected to the vertically extending portion of the substrate and a second, free end. A base plate extending substantially horizontally from a portion of the vertically extending portion of the substrate and spaced a distance below the free ends of the compliant membrane and back plate is further provided. A light source (e.g. a vertical-cavity surface-emitting laser (VCSEL)), positioned on the substrate, below the compliant membrane and back plate, is directed toward the grating of the back plate and reflective surface portion of the compliant membrane. A light detector may further be positioned on the substrate to detect a pattern of light reflected off of the compliant membrane and back plate grating (i.e. an interference pattern). The pattern represents a displacement of the compliant membrane caused by sound pressure waves, and therefore can be used to provide an indication of sound. In this aspect, the MEMS device uses a diffraction based optical interferometer method to provide an indication of sound. Circuitry may further be connected to the compliant membrane, the back plate, the base plate, the light emitter and/or the light detector.

During operation, application of a voltage by the circuitry causes electrostatic forces between the compliant membrane, the back plate and the base plate to tilt the compliant membrane and the back plate toward the base plate (which is stationary). In one embodiment, in the resting position (i.e. no voltage) the compliant membrane, the back plate and the base plate are substantially parallel to one another, in what may be described as a "horizontal" position. In the active position (i.e. voltage is applied), the free end of the back plate moves toward the base plate to tilt the back plate and set the tilt angle and the free end of the compliant membrane moves toward the back plate to tilt the compliant membrane. The tilt angle may be an acute angle, for example, less than 4 degrees, or for example, 3 degrees or less. In some embodiments, the tilt angle is a predetermined, set, angle such that the back plate and compliant membrane are either tilted at the set tilt angle or they are not tilted and in the horizontal position. In other embodiments, the tilt angle can vary depending upon the voltage applied. In other words, the application of a smaller voltage will result in a different tilt angle (e.g. smaller tilt angle) then when a larger voltage is applied (e.g. larger tilt angle). Spacers or posts may further be provided between the compliant membrane, the back plate and the support arm to avoid stiction and define a controlled minimal stress region of operation for the compliant membrane.

A process for manufacturing a MEMS optical microphone may include providing a substrate and forming a base plate layer over the substrate. A back plate layer may be formed over the base plate layer and a compliant membrane layer may be formed over the back plate layer. A light emitter and a light detector may be connected to the substrate. In addition, directional circuitry may be connected to the base plate layer, the back plate layer and the compliant membrane layer. The circuitry is operable to cause the back plate layer and the compliant membrane layer to tilt with respect to the base plate layer when a voltage is applied so as to modify an alignment between a reflective portion of the compliant membrane layer and the light source and direct the reflected light toward the light detector. In some embodiments, prior to forming the base plate layer, the back plate layer and the compliant membrane layer, a sacrificial layer is formed between each layer to define a gap between each of the layers, and then subsequently removed. Each of the layers may be formed using MEMS processing techniques.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments are illustrated by way of example and not by way of limitation in the figures of the accompanying drawings in which like references indicate similar elements. It should be noted that references to "an" or "one" embodiment in this disclosure are not necessarily to the same embodiment, and they mean at least one.

DETAILED DESCRIPTION

In this section we shall explain several preferred embodiments of this invention with reference to the appended drawings. Whenever the shapes, relative positions and other aspects of the parts described in the embodiments are not clearly defined, the scope of the invention is not limited only to the parts shown, which are meant merely for the purpose of illustration. Also, while numerous details are set forth, it is understood that some embodiments of the invention may be practiced without these details. In other instances, well-known structures and techniques have not been shown in detail so as not to obscure the understanding of this description.

Figure 1A:
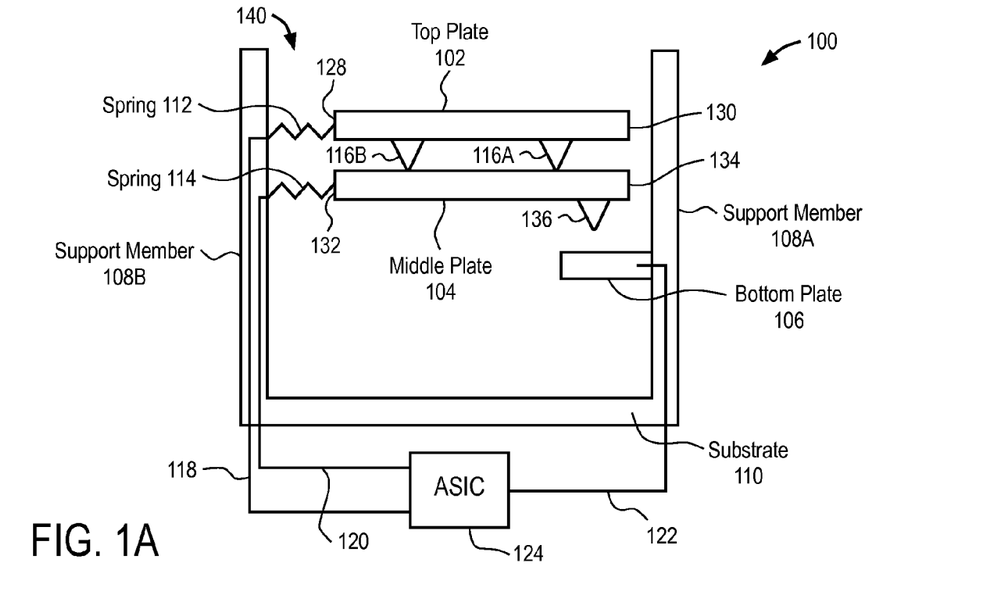
FIG. 1A illustrates a cross-sectional side view of one embodiment of a MEMS device.

FIG. 1A illustrates a cross-sectional side view of one embodiment of a MEMS device. MEMS device 100 may, in some embodiments, be any type of MEMS sensor that can benefit from being able to tilt one or more plates or layers within the sensor as described herein. For example, MEMS device 100 may be an optical microphone, an inertial sensor, an accelerometer, a gyrometer or the like. Representatively, in one embodiment, device 100 includes a top plate 102, a middle plate 104 and a bottom plate 106. Each of top plate 102, middle plate 104 and bottom plate 106 may be parallel to one another in one state, and extend horizontally from vertically extending support members 108A or 108B of substrate 110 (i.e. top plate 102, middle plate 104 and bottom plate 106 are perpendicular to support members 108A-108B). In one embodiment, vertically extending support members 108A and 108B may be sidewalls of a cavity 140 which is pre-formed within substrate 110 before each of top plate 102, middle plate 104 and bottom plate 106 are formed using MEMS processing techniques (e.g. deposition processes, patterning, lithography, etching, etc.).

In one embodiment, top plate 102 is attached at one end 128 to vertically extending support member 108B by a spring 112, or other similar structure that allows for movement of top plate 102 with respect to support member 108B. The other end of top plate 102 is a free end 130 that is not directly connected to another structure (e.g., the free end 130 is not connected to support member 108A). Similarly, middle plate 104 is attached at one end 132 to support member 108B by a spring 114 and the other end is a free end 134 that is not directly connected to another structure. Top plate 102 and middle plate 104 may have a similar length, which is slightly less than the distance between support member 108A and 108B. Middle plate 104 is spaced a distance below top plate 102 by spacers 116A and 116B. Spacers 116A and 116B may be formed on a bottom side of top plate 102, or a top side of middle plate 104, such that they space one plate from the other.

Bottom plate 106 extends from vertically extending support member 108A, in a direction toward support member 108B. Middle plate 104 is spaced a distance from bottom plate 106 by spacer 136. Unlike top plate 102 and middle plate 104, bottom plate 106 is a stationary structure which is fixedly attached to support member 108B. In some embodiments, bottom plate 106 has a length which is shorter than a length of top plate 102 and middle plate 104. For example, bottom plate 106 extends a distance from support member 108A such that it is beneath the free ends 130, 134 of top plate 102 and middle plate 104, but less than the entire length of top plate 102 and bottom plate 104. In other embodiments, bottom plate 106 may extend from support member 108B, in a direction of support member 108A, and in some cases, extend all the way to support member 108A such that both ends are fixed to respective support members 108A-108B. In each embodiment, it is important that bottom plate 106 have a length sufficient provide a fixed support surface below middle plate 104 for tilting of middle plate 104.

Device 100 may further include a circuit 124 (e.g. an application specific integrated circuit (ASIC)) electrically connected to top plate 102, middle plate 104 and bottom plate 106 by wiring 118, 120 and 122, respectively. Wiring 118, 120 and 122 may run through substrate 110 and support members 108A-108B to the respective plates 102, 104 and 106. In one embodiment, circuit 124 may be configured to receive power from an external source and apply a voltage to one or more of top plate 102, middle plate 104 and bottom plate 106. The application of a voltage to one or more of top plate 102, middle plate 104 and bottom plate 106 can be used to tilt the plates from the resting, and in this example horizontal, position shown in FIG. 1A.

Figure 1B:
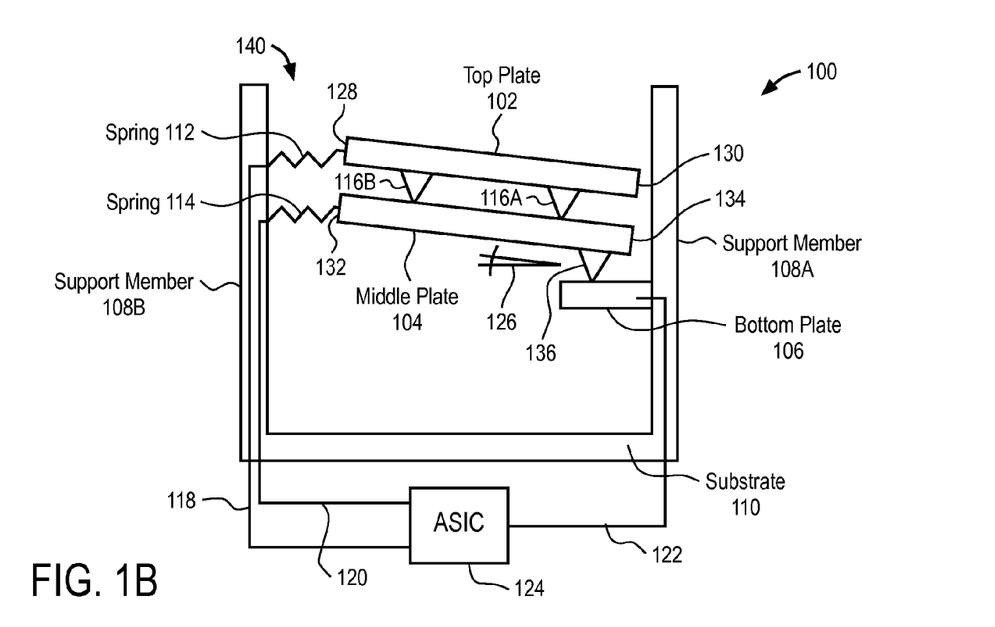
FIG. 1B illustrates the MEMS device of FIG. 1A in a tilted configuration.

FIG. 1B illustrates the MEMS device of FIG. 1A in a tilted configuration. Representatively, the application of the voltage to one or more of top plate 102, middle plate 104 and bottom plate 106 through circuit 124 creates electrostatic forces between each plate which cause the plates to be drawn toward one another. In other words, top plate 102, middle plate 104 and bottom plate 106 act as electrodes which are electrically isolated from one another by spacers 116A, 116B, 136 such that capacitors are formed between each of the plates. Therefore, when the appropriate voltage is applied to each of top plate 102, middle plate 104 and bottom plate 106, the resulting electrostatic forces cause them to become clamped together. In one embodiment, the voltage can be applied as a direct current (DC) voltage. Alternatively, the voltage can be an alternating current (AC) voltage. Since end 128 of top plate 102 and end 132 of middle plate 104 are connected to support member 108B by springs 112 and 114, respectively, the greatest degree of movement occurs at free ends 130, 134. Still further, since bottom plate 106 is stationary, free end 130 of top plate 102 and free end 134 of middle plate 104 move toward bottom plate 106 resulting in top plate 102 and middle plate 104 having a tilted configuration in which ends 128, 132 are higher than free ends 130, 134.

Representatively, when the appropriate voltage is applied to each of top plate 102, middle plate 104 and bottom plate 106, the free end 134 of the middle plate 104 moves toward the bottom plate 106 (which is stationary) to tilt the middle plate 104 and set the tilt angle 126. In addition, the free end 130 of top plate 102 moves toward middle plate 104 to tilt the top plate 102. In this aspect, top plate 102 and middle plate 104 can be accurately tilted to an optimal and fine tuned tilt angle 126, which provides a desired device performance (e.g. directs light reflected off the plates toward a detector). For example, in one embodiment, the angle 126 may be an acute angle, for example, less than 4 degrees, for example, 3 degrees or less. It is further to be understood that spacers 116A, 116B and 136 are dimensioned to maintain an even space or gap between top plate 102, middle plate 104 and bottom plate 106 so that stiction between the plates is avoided and a controlled minimal stress region of operation between top plate 102 and middle plate 104 can be maintained. In this aspect, a device which is formed using MEMS processing techniques is provided which includes components (e.g. plates) that can be tilted from an otherwise horizontal orientation typically found in MEMS devices.

Figure 2A:
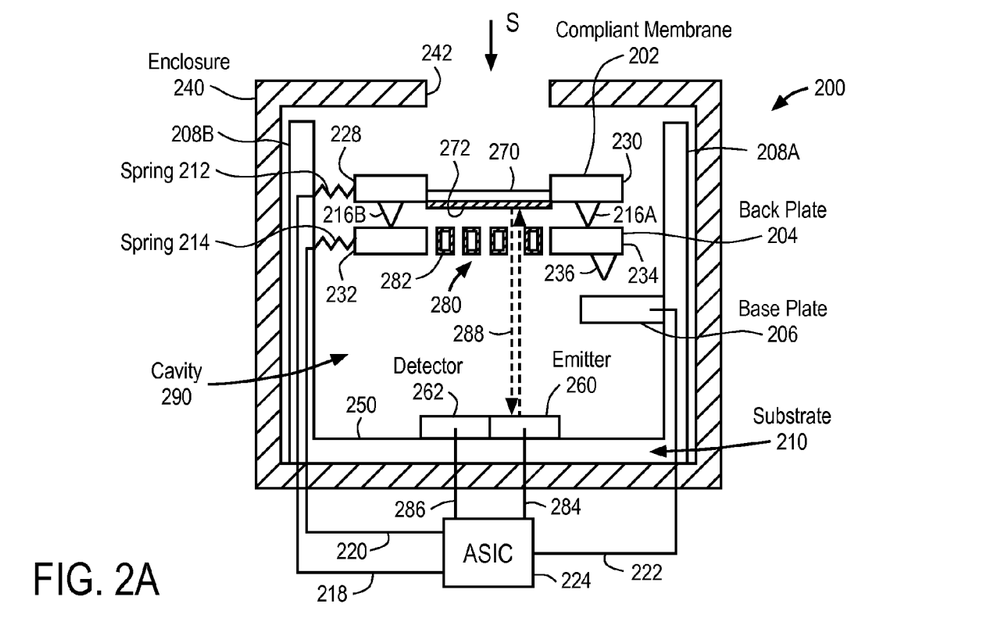
FIG. 2A illustrates a cross-sectional side view of one embodiment of a MEMS optical microphone.

FIG. 2A illustrates a cross-sectional side view of another embodiment of a MEMS device. In this embodiment, the MEMS device is a MEMS optical microphone 200. In this aspect, since the MEMS device is an optical microphone, each of the previously discussed plates 102, 104 and 106, although operable in the manner previously discussed, are manufactured using MEMS processing techniques to carry out the functions of an optical microphone. Representatively, microphone 200 may include a top plate such as compliant membrane 202, a middle plate such as back plate 204, a bottom plate such as base plate 206, an emitter 260 and a detector 262. Each of compliant membrane 202, back plate 204, base plate 206, and in some cases emitter 260 and detector 262, may be built on substrate 210 using MEMS processing techniques. Substrate 210 may be mounted within a frame or enclosure 240. Enclosure 240 may include an acoustic port 242 through which sound (S) (also referred to as acoustic waves) can travel into microphone 200. Although acoustic port 242 is illustrated along a top side of enclosure 240, it could also be along a bottom side or side wall of enclosure 240 (while still allowing the acoustic waves to reach the compliant membrane 202) and therefore is not limited to the illustrated location.

Compliant membrane 202 may be configured to vibrate in response to sound (S) (acoustic waves) entering enclosure 240 through acoustic port 242. In this aspect, compliant membrane 202 may also be referred to as a diaphragm. Compliant membrane 202 may be made of any material and have any dimensions suitable to provide a semi-rigid or compliant membrane that vibrates in response to sound waves, for example, polysilicon. In addition, compliant membrane 202 may be made of, or have a material integrated therein, that allows for compliant membrane 202 to function as an electrode. In some embodiments, a center portion 270 of compliant membrane 202 may be considered the portion that vibrates while the outer portions primarily serve as a rigid frame to support center portion 270 as will be discussed in more detail in reference to FIG. 3. In this aspect, the center portion 270 may be more compliant than the outer portions.

In addition, a reflective surface 272 may be formed on a side of center portion 270 facing emitter 260 and detector 262 such that a vibration of center portion 270 can be detected by reflecting a light emitted by emitter 260 toward detector 262. In some embodiments, the center portion 270 is made of a reflective material (e.g. metallic foil) while in other embodiments, the reflective surface 272 is formed by application of a coating (e.g. metal coating such as gold) to center portion 270. Although reflective surface 272 is shown positioned only within center portion 270, it is contemplated that the reflective surface may extend beyond center portion, for example, to the ends 230, 228 of compliant membrane 202. Compliant membrane 202, including center portion 270 and reflective surface 272, may be built upon substrate 210 using MEMS processing techniques (e.g. deposition processes, patterning, lithography, etching, etc.).

Back plate 204 may be a substantially rigid plate positioned between compliant membrane 202 and emitter 260 and detector 262. For example, back plate 204 may be made of a thick and stiff silicon plate. In addition, back plate 204 may be made of, or have a material integrated therein, that allows for back plate 204 to function as an electrode that can be tilted as described herein. Back plate 204 may include a grating 280 aligned with emitter 260 and detector 262 such that light directed toward reflective surface 272 and light reflected from reflective surface 272 passes through grating 280. Grating 280 is dimensioned to form an interference pattern which can be detected by detector 262 and used as an indicator of a movement of compliant membrane 202. Since the pattern represents a displacement of the compliant membrane 202, it can be used to provide an indication of sound using a diffraction based optical interferometer method or any other optical interferometric method. Representatively, in some embodiments, grating 280 may also include a reflective coating 282 to facilitate formation of the interference pattern. Back plate 204, including grating 280, may be built upon substrate 210 using MEMS processing techniques (e.g. deposition processes, patterning, lithography, etching, etc.).

Base plate 206 may be a substantially rigid plate positioned between back plate 204 and emitter 260 and detector 262. Base plate 206 may be a fixed structure that is built upon substrate 210 using MEMS processing techniques (e.g. deposition processes, patterning, lithography, etching, etc.). In this aspect, base plate may be made of a similar material, or different material, as back plate 204, for example, a silicon material.

In one embodiment, in their untilted state, each of compliant membrane 202, back plate 204 and base plate 206 are parallel to one another and extend in a direction perpendicular to vertically extending support members 208A or 208B (e.g. horizontally). Vertically extending support members 208A and 208B may be members which extend in a direction perpendicular to a horizontal base portion 250 of substrate 210. Vertically extending support members 208A and 208B may be pre-formed portions of substrate 210 (i.e. sidewalls of a cavity 290 formed within substrate 210) or formed on top of substrate 210 using MEMS techniques.

Compliant membrane 202 is attached at one end 228 to vertically extending support member 208B by a spring 212, or other similar structure that allows for a pivot or hinge type movement of compliant membrane 202 with respect to support member 208B. Representatively, spring 212 may be a tension/extension spring, a flat spring, a corrugated structure, or an arm member which has some degree of elasticity to allow for compliant membrane 202 to be tilted without interfering with a vibration of compliant membrane 202 in response to sound waves. The other end of compliant membrane 202 is a free end 230 that is not directly connected to another structure (e.g., the free end is not connected to support member 208A). In this aspect, free end 230 is free to move up or down while a vertical position of end 228 along support member 208B remains substantially the same. Compliant membrane 202 may have a length which is slightly less than a distance between support member 208A and 208B such that it can be tilted between members 208A and 208B.

Back plate 204 is attached at one end 232 to support member 208B. Back plate 204 may be attached to support member 208B at a position below end 228 of compliant membrane 202 such that back plate 204 is between compliant membrane 202 and base plate 206. End 232 of back plate 204 may be attached to support member 208B by a spring 214. Spring 214 may be similar to spring 212. The other end of back plate 204 is a free end 234 that is not directly connected to another structure (e.g. not directly connected to support member 208B). In this aspect, free end 234 is free to move up or down while a vertical position of end 232 along support member 208B remains substantially the same such that back plate 204 can be tilted similar to compliant membrane 202. Back plate 204 may have a length which is slightly less than a distance between support member 208A and 208B such that it can be tilted between members 208A and 208B.

Compliant membrane 202 is spaced a distance from back plate 204 by spacers 216A and 216B. Spacers 216A and 216B may be attached to a bottom surface of compliant membrane 202 or a top surface of back plate 204. Spacers 216A and 216B may be of a dimension and material which allows them to both mechanically and electrically isolate compliant membrane 202 from back plate 204. Representatively, spacers 216A and 216B may be made of an insulating material, for example, porcelain (ceramic), glass, mica, plastics, and the oxides of various metals.

Base plate 206 extends from vertically extending support member 208A, in a direction toward support member 208B. Base plate 206 may be at a position along support member 208A which is below back plate 204 such that base plate 206 is between back plate 204 and substrate 210. Base plate 206 is positioned a distance from back plate 204 by spacer 236. Spacer 236 may be attached to one of a bottom side of back plate 204 or a top side of base plate 206 and be of a dimension and material such that it both mechanically and electrically isolates back plate 204 from base plate 206. Representatively, spacer 236 may be made of an insulating material (e.g., porcelain (ceramic), glass, mica, plastics, and the oxides of various metals).

Unlike compliant membrane 202 and back plate 204, base plate 206 is a stationary structure which is fixedly attached to support member 208B. In some embodiments, base plate 206 has a length which is shorter than a length of compliant membrane 202 and back plate 204. For example, base plate 206 extends a distance from support member 208A such that it is beneath the free ends 230, 234 of compliant membrane 202 and back plate 204, but not beneath the entire length of compliant membrane 202 and base plate 204. In other embodiments, base plate 206 extends from support member 208A to support member 208B such that it extends the entire distance between support members 208A-208B and, in some cases, is fixed at both ends to the respective support member 208A-208B.

Device 200 may further include a circuit 224 (e.g. an application specific integrated circuit (ASIC)) attached to compliant membrane 202, back plate 204 and base plate 206 by wiring 218, 220 and 222, respectively. Wiring 218, 220 and 222 may run through substrate 210 and support members 208A-208B to the respective one of membrane 202, back plate 204 and base plate 206. In one embodiment, the circuit 224 may be configured to receive power from an external source and apply a voltage to one or more of compliant membrane 202, back plate 204 and base plate 206. The application of a voltage to one or more of compliant membrane 202, back plate 204 and base plate 206 can be used to tilt the plates from the otherwise horizontal position shown in FIG. 2A. When the voltage is removed, compliant membrane 202, back plate 204 and base plate 206 may return to the resting position (i.e. horizontal position).

In addition, circuit 224 may be connected to emitter 260 and detector 262 by wiring 284, 286, respectively. Wiring 284, 286 may run through substrate 210 and support members 208A-208B to emitter 260 and/or detector 262. In this aspect, circuit 224 may receive power from an external source and provide power to emitter 260 and/or detector 262. In some embodiments, emitter 260 may be a light source such as a VCSEL that is electrically connected to substrate 210. Emitter 260 may be configured to emit a laser light (or beam) in the direction of grating 280 and reflector 282, for detection by detector 262. Detector 262 may, in some embodiments, be a photo detector configured to detect a reflected light (or beam) generated by emitter 260. The emitter 260 (e.g. VCSEL) and detector 262 (e.g. photo detector) can be off the shelf commercially available parts or custom built for a specific implementation.

Figure 2B:
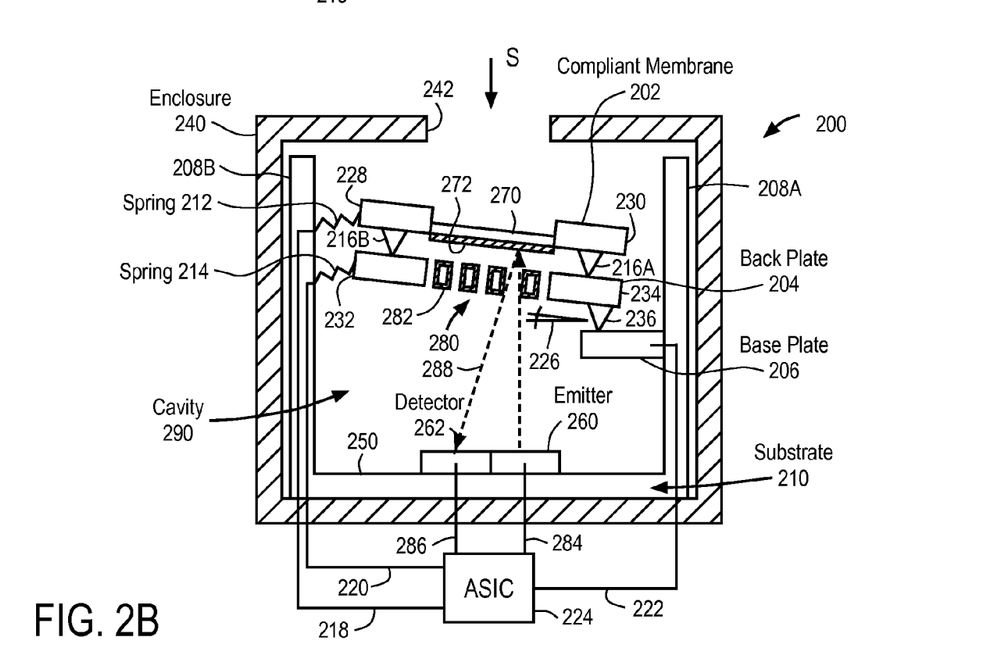
FIG. 2B illustrates the optical microphone of FIG. 2A in a tilted configuration.

Each of compliant membrane 202, back plate 204 and base plate 206 are parallel to one another and substantially planar structures which are manufactured in a horizontal configuration. Emitter 260 is directly below compliant membrane 202 and back plate 204 such that light emitted from emitter 260 is directed "straight on" toward compliant membrane 202 and back plate 204. In this configuration, however, the light will reflect off of reflective surface 272 of compliant membrane 202 back to emitter 260, not detector 262, as illustrated by dashed arrow 288. In this aspect, to properly align the reflected light and direct the light to detector 262, compliant membrane 202 and back plate 204 are tilted as illustrated in FIG. 2B. It is noted that the light is directed by tilting only compliant membrane 202 and back plate 204, not emitter 260, detector 262 and/or substrate 210 thus providing a microphone which can be mass produced using MEMS processing techniques and without adding tolerances associated with, for example, positioning emitter 260 and/or detector 262 at an angle.

As can be seen from FIG. 2B, tilting of compliant membrane 202 and base plate 204, causes reflected light 288 to be directed toward detector 262. Representatively, during operation, a voltage is applied to compliant membrane 202, back plate 204 and base plate 206 through circuit 224. The voltage creates electrostatic forces between each plate causing them to be drawn toward one another. In other words, compliant membrane 202, back plate 204 and base plate 206 act as electrodes which are electrically isolated from one another by spacers 216A, 216B and 236 such that capacitors are formed between each of the plates. Therefore, when the voltage is applied to each of compliant membrane 202, back plate 204 and base plate 206, the electrostatic forces cause them to become clamped together. In one embodiment, the voltage can be applied as a direct current (DC). Alternatively, the voltage can be an alternating current (AC). Since one end 228, 232 of compliant membrane 202 and back plate 204, respectively, are maintained at a vertical position along support member 208B by springs 212 and 214, respectively, only their free ends 230, 234 move toward one another. Still further, since base plate 206 is stationary, free ends 230, 234 of compliant membrane 202 and back plate 204, respectively, move toward base plate 206 resulting in compliant membrane 202 and back plate 204 having a tilted configuration.

Representatively, when the voltage is applied to one or more of compliant membrane 202, back plate 204 and base plate 206, the free end 234 of the back plate 204 moves toward the base plate 206 (which is stationary) to tilt the back plate 204 and set the tilt angle 226. In some embodiments, spacer 236 rests on base plate 206 to set a fixed tilt angle 226. The free end 230 of compliant membrane 202, in turn, moves toward back plate 204 to tilt the compliant membrane 202. In some embodiments, spacers 216A-216B rest on back plate 204 such that compliant membrane 202 is at the same angle as back plate 204. In this aspect, compliant membrane 202 and back plate 204 can be tilted to an optimal and fine tuned tilt angle 226, which provides a desired device performance (e.g. directs reflected light toward detector 262). For example, in one embodiment, the angle 226 may be an acute angle, for example, less than 4 degrees, for example, 3 degrees or less. It is further contemplated that in some embodiments, different, or intermediate, tilt angles may be achieved depending, for example, upon a voltage applied to the circuitry 224. For example, in some embodiments, the application of a smaller voltage causes back plate 204 to tilt toward, but not touch, base plate 206, thus resulting in a smaller tilt angle being set by back plate 204. The application of a larger voltage will, in turn, draw back plate 204 closer to base plate 206, thus resulting in a larger tilt angle being set by back plate 204. Application of a similar voltage to compliant membrane 202 will then cause compliant membrane 202 to tilt to the same angle as back plate 204. It is further to be understood that spacers 216A, 216B and 234 are dimensioned to maintain an even, space or gap between compliant membrane 202, back plate 204 and base plate 206 so that stiction between the plates is avoided and a controlled minimal stress region of operation between compliant membrane 202 and back plate 204 can be maintained.

Detector 262 then detects the reflected light 288 and provides an indication of sound. In particular, compliant membrane 202 vibrates in response to sound (S). The vibration of compliant membrane 202 modulates an intensity of light 288 reflected off of the reflective surface 272 of compliant membrane 202. In addition, movement of compliant membrane 202 with respect to grating 280 (which is rigid) causes an interference pattern formed by grating 280 to change in size. This modulation in intensity (i.e. change in size of the interference pattern) is detected by detector 262 and used as an indication of the movement of membrane 202 and in turn, provides an indication of sound. It is further to be understood that in order to determine sound from the interference pattern, a distance between compliant membrane 202 and back plate 204 is set such that it is an integer multiple of ¼ λ of the light 288.

Figure 3:
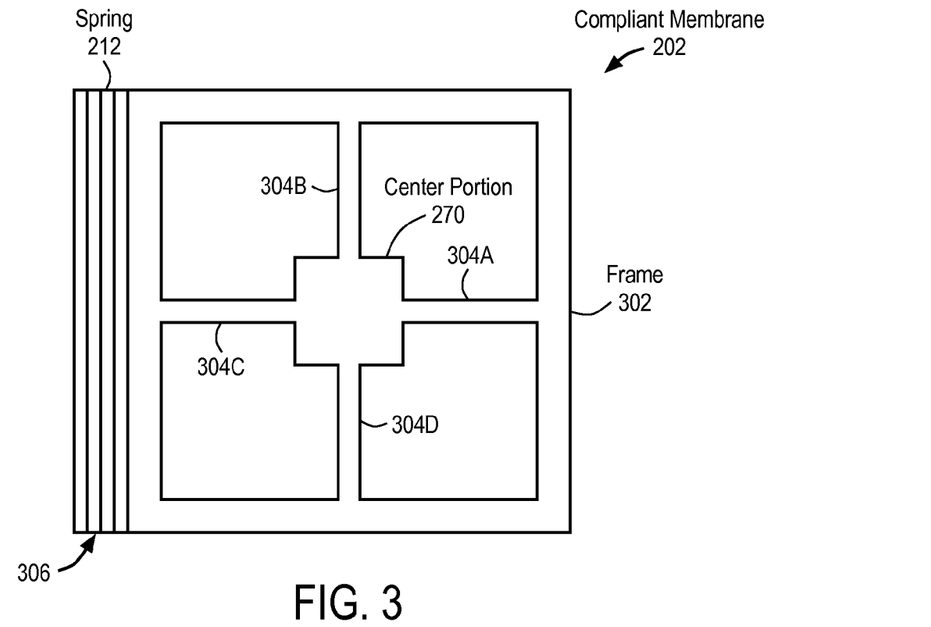
FIG. 3 illustrates a top view of the compliant membrane of the optical microphone of FIG. 2A.

FIG. 3 illustrates a top view of the compliant membrane of the optical microphone of FIG. 2A. From this view, it can be seen that compliant membrane 202 may have a center portion 270 suspended within an outer frame 302 by spokes 304A, 304B, 304C and 304D. Center portion 270 may be a compliant membrane configured to vibrate in response to acoustic or sound waves while spokes 304A-304D and frame 302 are substantially rigid. In this aspect, center portion 270 may be considered the primary sound pick up surface area of compliant membrane 202 which is used to detect sound while the outer portions (spokes 304A-304D and/or frame 302) are used to suspend the center portion 270 in the desired location. In some embodiments, center portion 270, spokes 304A-304D and frame 302 are made from a single material layer using MEMS processing techniques. In one embodiment, center portion 270 is thinner (in the z-height direction) than spokes 304A-304D and frame 302 such that center portion 270 is considered compliant (can vibrate in response to acoustic waves) while outer portions (spokes 304A-304D and frame 302) are substantially rigid and unresponsive to acoustic waves.

In one embodiment, center portion 270 is a substantially square shaped membrane having dimensions sufficient to achieve a desired acoustic vibration. In other embodiments, center portion 270 may have any type of quadrilateral shape, or other shapes, for example, a circle, ellipse, oval or the like. In the case of a square shaped center portion 270, each of spokes 304A-304D may extend from a respective side of center portion 270 to frame 302. Membrane frame 302, may in turn, be a square shaped structure. Each of the sides of frame 302 may run parallel to a respective side of center portion 270. In other embodiments, spokes 304A-304D and frame 302 may be oriented in any manner with respect to center portion 270 that is sufficient to suspend center portion 270 above back plate 204, base plate 206 and emitter 260/detector 262 as previously discussed.

Spring 212 runs along one side of frame 302 so that it can be used to attach frame 302 to support member 208B as discussed in reference to FIG. 2A. Spring 212 can run along an entire length of the side of frame 302, or less than the entire length. Spring 212 can be made from the same material layer used to form compliant membrane 202 such that it is integrally formed with compliant membrane 202 using MEMS processing techniques. For example, frame 302 may be wider on the side where it is desirable to have spring 212. Corrugations 306 may then be formed in the extra width portion of frame 302 to form an elastic structure that functions as a spring. In other embodiments, spring 212 may have any structure sufficient to suspend complaint membrane 202 from support member 208B and allow compliant membrane 202 to tilt as previously discussed in reference to FIG. 2B.

Figure 4:
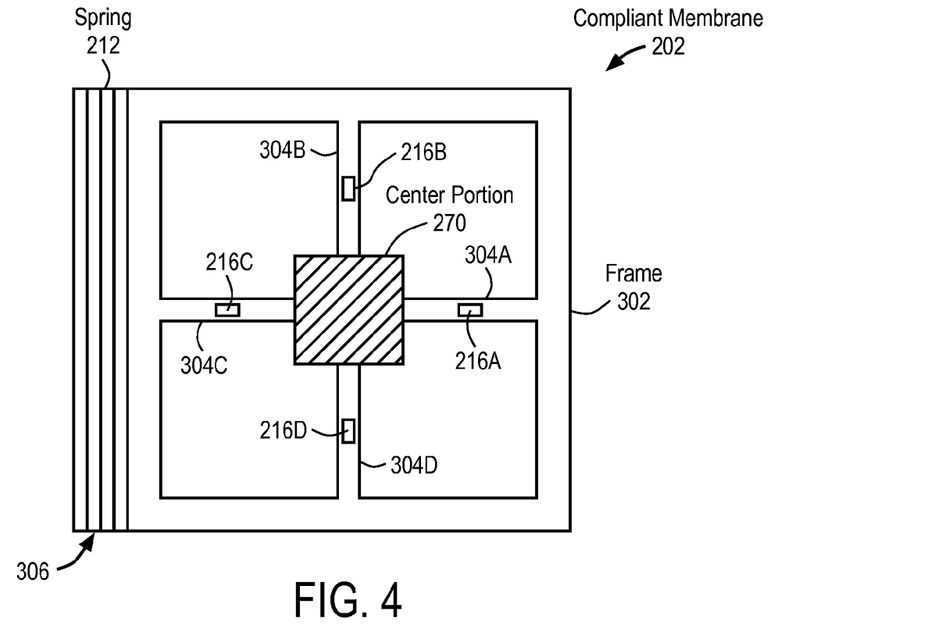
FIG. 4 illustrates a bottom view of the compliant membrane of FIG. 3.

FIG. 4 illustrates a bottom view of the compliant membrane of FIG. 3. From this view, it can be seen that the bottom surface of center portion 270 includes a reflective surface 272. In some embodiments, reflective surface 272 is confined to only the area of center portion 270 since this is the sound pick up area of compliant membrane 202, and therefore the portion used to provide an indication of sound. In other embodiments, reflective surface 272 is formed along the entire bottom side of compliant membrane 202 (e.g., also along spokes 304A-304D and/or frame 302). For example, in embodiments where reflective surface 272 is a coating (e.g. a gold coating), it may be applied along the entire bottom side of compliant membrane 202.

Spacers 216A, 216B, 216C and 216D are also shown positioned along the bottom side of compliant membrane 202. Although four spacers 216A-216D are shown positioned along each of spokes 304A-304D, respectively, it is contemplated that any number of spacers may be provided and they may be positioned along any portion of the bottom side of compliant membrane 202 sufficient to space compliant membrane 202 a distance from back plate 204. Spacers 216A-216D may further have any size and shape suitable for spacing compliant membrane 202 a distance from back plate 204. Representatively, spacers 216A-216D may be cone, pyramid, cube, or hemispherically shaped structures. Spacers 216A-216D should be of any material sufficient to both mechanically and electrically isolate compliant membrane 202 a distance from back plate 204. For example, spacers 216A-216D may be made of an insulating material as previously discussed. In one embodiment, spacers 216A-216D may be formed from a different material layer than compliant membrane 202 using MEMS processing techniques.

Figure 5:
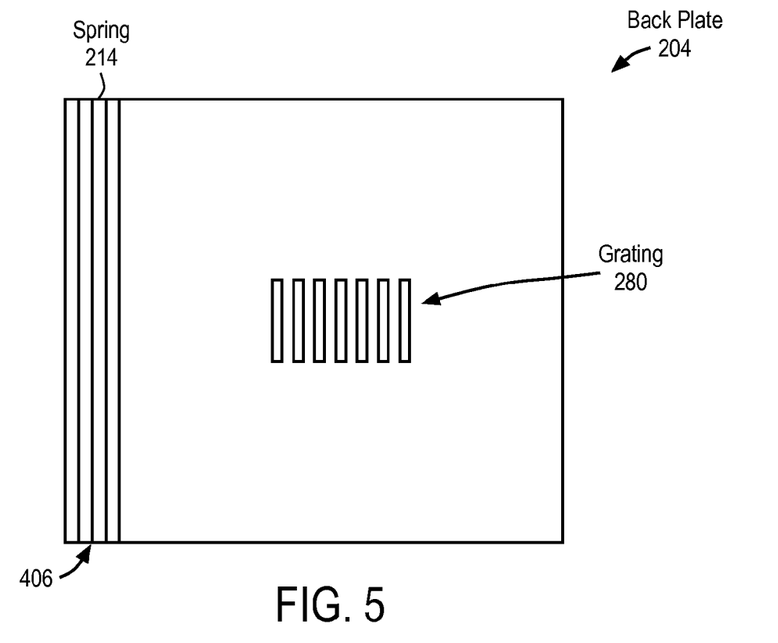
FIG. 5 illustrates a top view of a back plate of the optical microphone of FIG. 2A.

FIG. 5 illustrates a top view of a back plate of the optical microphone of FIG. 2A. Back plate 204 may be a substantially rigid plate having grating 280, which can be formed therein by MEMS processing techniques. Back plate 204 may have a similar size and shape as compliant membrane 202, for example a square shape. Alternatively, back plate 204 may have any type of quadrilateral shape, or other shapes, for example, a circle, ellipse, oval or the like. Grating 280 may have a periodic structure sufficient to split and diffract light emitted from an emitter (e.g. emitter 260) into different beams for detection by a detector (e.g. detector 262). In some embodiments, the grating 280 causes the formation of an interference pattern which can be used to indicate a movement of compliant membrane 202 in response to sound waves, and in turn, as an indicator of sound. Grating 280 may be formed in a portion of back plate 204 which is aligned with center portion 270 of compliant membrane 202 and emitter 260/detector 262, as described in FIG. 2A. In the illustrated embodiment, grating 280 is formed in a center portion of back plate 204 which, when microphone 200 is assembled, causes grating 280 to be positioned between center portion 270 of compliant membrane 202 and emitter 260/detector 262.

Spring 214 runs along one side of back plate 204 so that it can be used to attach back plate 204 to support member 208B as discussed in reference to FIG. 2A. Spring 214 can run along an entire length of the side of back plate 204 or less than the entire length. Spring 214 can be made from the same material layer used to form back plate 204 such that it is integrally formed with back plate 204 using MEMS processing techniques. For example, back plate 204 may be wider on the side where it is desirable to have spring 214. Corrugations 406 may then be formed in the extra width portion of back plate 204 to form an elastic structure that functions as a spring. In other embodiments, spring 214 may have any structure sufficient to suspend back plate 204 from support member 208B and allow back plate 204 to tilt as previously discussed in reference to FIG. 2B.

Figure 6:
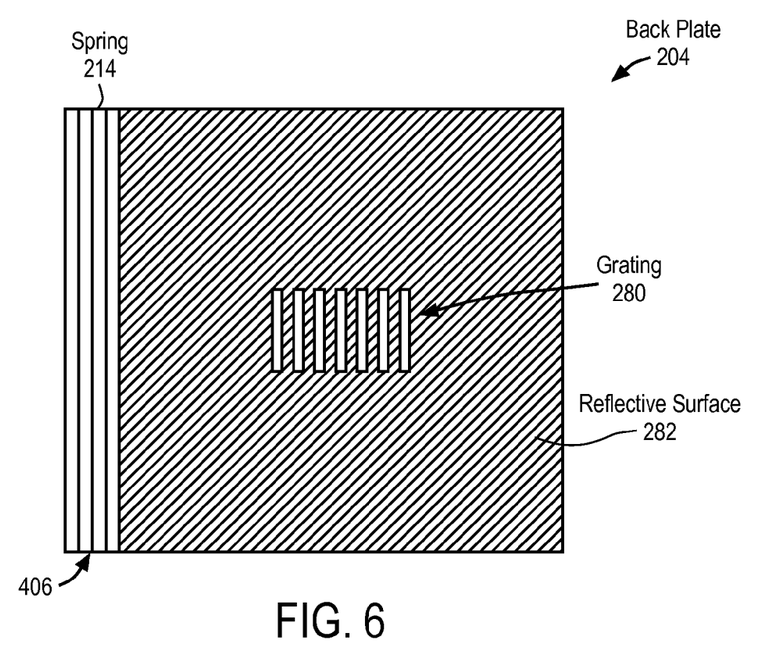
FIG. 6 illustrates a bottom view of the back plate of FIG. 5.

FIG. 6 illustrates a bottom view of the back plate of FIG. 5. From this view, it can be seen that back plate 204 includes a reflective layer 282 along its bottom side. Reflective layer 282 may also, in some embodiments, be formed along the top side of back plate 204. For example, reflective layer 282 may be formed along all surfaces of grating 280 to form a grating which is reflective from all angles. Reflective layer 282 may be a material layer, which is formed on back plate 204, or a coating (e.g. a gold coating) which is applied to one or more surfaces of back plate 204. Alternatively, back plate 204 may be made of a reflective material such that any outer surfaces of back plate 204 are reflective.

Figure 7A:
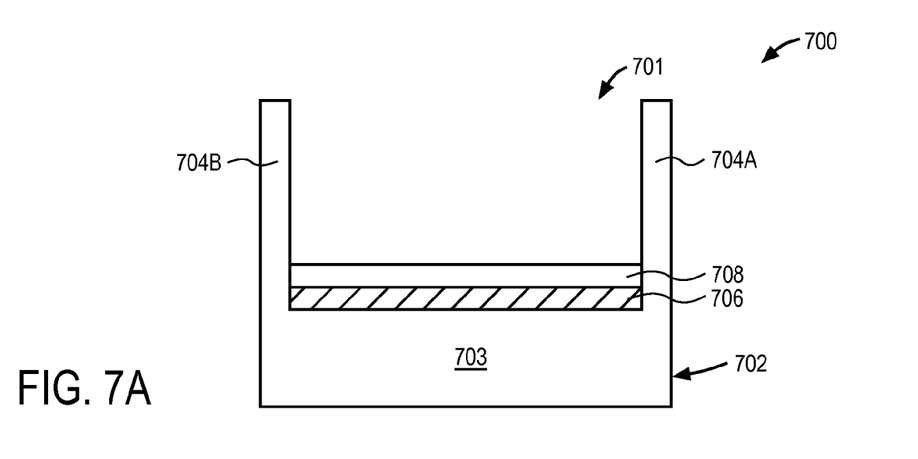
FIG. 7A illustrates one embodiment of a processing step for fabricating the optical microphone of FIG. 2A.

FIG. 7A illustrates one embodiment of a processing step for fabricating the optical microphone of FIG. 2A. FIG. 7A illustrates substrate 702 having a cavity 701 formed therein. Substrate 702 may be a silicon substrate, for example, a silicon on insulator (SOI) wafer. Cavity 701 may be defined by vertically extending support member 704A and vertically extending support member 704B and a base portion 703 of substrate 702. In one embodiment, cavity 701 is formed within substrate 702 using a MEMS etching process, for example, reactive ion etching (RIE). Alternatively, cavity 701 may be formed on top of substrate 702 by stacking additional material layers and then patterning the layers to form cavity 701. MEMS microphone 200 may be formed within cavity 701.

Representatively, in one embodiment, a sacrificial layer 706 may be formed on top of the base portion 703 of substrate 702. Sacrificial layer 706 may be formed by any MEMS processing technique suitable for forming a sacrificial layer. For example, sacrificial layer 706 may be formed by blanket depositing a sacrificial material over substrate 702 using a chemical vapor deposition (CVD) process and then planarizing the layer to provide a desired layer thickness. Sacrificial layer 706 may be made of any material that can be selectively removed or patterned using MEMS processing steps. Representatively, sacrificial layer 706 may be made of silicon dioxide or a silicate glass.

Base plate layer 708 may be formed over sacrificial layer 706. Base plate layer 708 may be formed by any MEMS processing technique suitable for forming a base plate layer, for example, blanket depositing a base plate layer material using CVD. Base plate layer 708 may be made of any material suitable for forming, for example base plate 206 previously discussed in reference to FIG. 2A. Representatively, base plate layer 708 may be made of a silicon material.

Figure 7B:
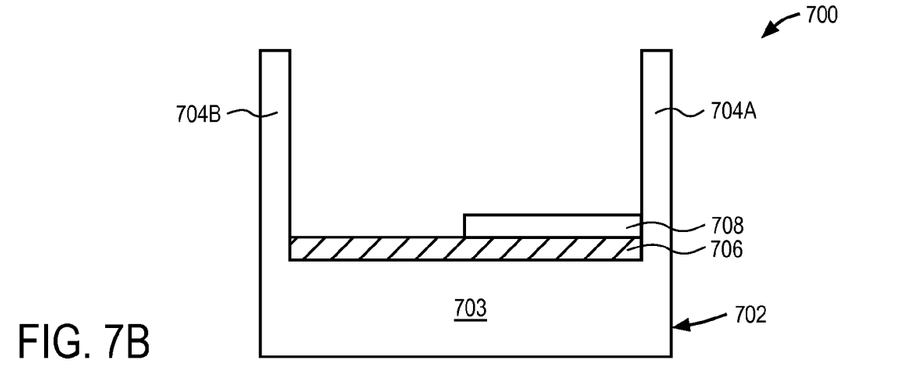
FIG. 7B illustrates one embodiment of another processing step for fabricating the optical microphone of FIG. 2A.

FIG. 7B illustrates one embodiment of another processing step for fabricating the optical microphone of FIG. 2A. FIG. 7B shows base plate layer 708 after a processing step in which portions of base plate layer 708 are removed to form a structure suitable for use as a base plate within microphone 200. For example, base plate layer 708 may be patterned using different etching steps (e.g. reactive ion etching) to have the shape and dimensions of base plate 206 described in reference to FIG. 2A. Since base plate layer 708 is to be used as the base structure which supports the tilt of other plates (or membranes) (e.g. membrane 202 and back plate 204 discussed in reference to FIG. 2A), sacrificial layer 706 should have a thickness equal to the desired distance or gap between the base plate of the microphone and the substrate (e.g. substrate 210) so that when sacrificial layer 706 is removed a space or gap of the desired size remains between the structures.

Figure 7C:
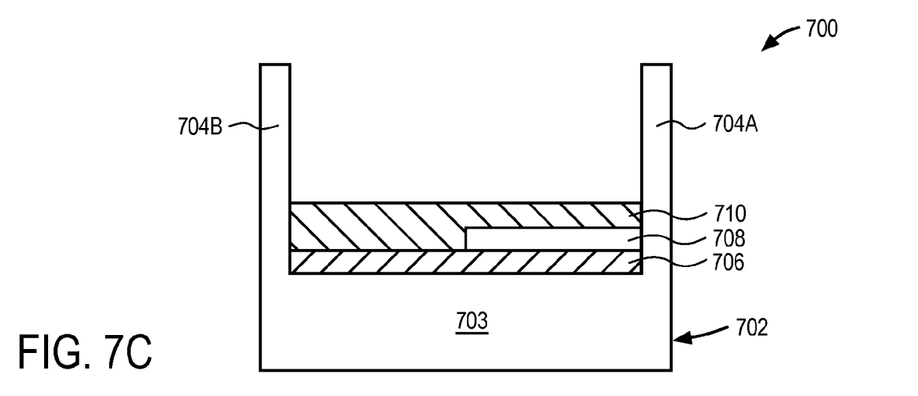
FIG. 7C illustrates one embodiment of another processing step for fabricating the optical microphone of FIG. 2A.

FIG. 7C illustrates one embodiment of another processing step for fabricating the optical microphone of FIG. 2A. FIG. 7C illustrates the step of forming a sacrificial layer 710 over base plate layer 708. Sacrificial layer 710 may be formed using any MEMS processing step suitable for forming a sacrificial layer over another layer. For example, sacrificial layer 710 may be formed by blanket depositing a sacrificial layer material over base plate layer 708 and sacrificial layer 706 using CVD. Sacrificial layer 710 may be substantially similar to sacrificial layer 706. Sacrificial layer 708 may be of any material that can be selectively removed during a further processing step (e.g. silicon dioxide or silicate glass).

Figure 7D:
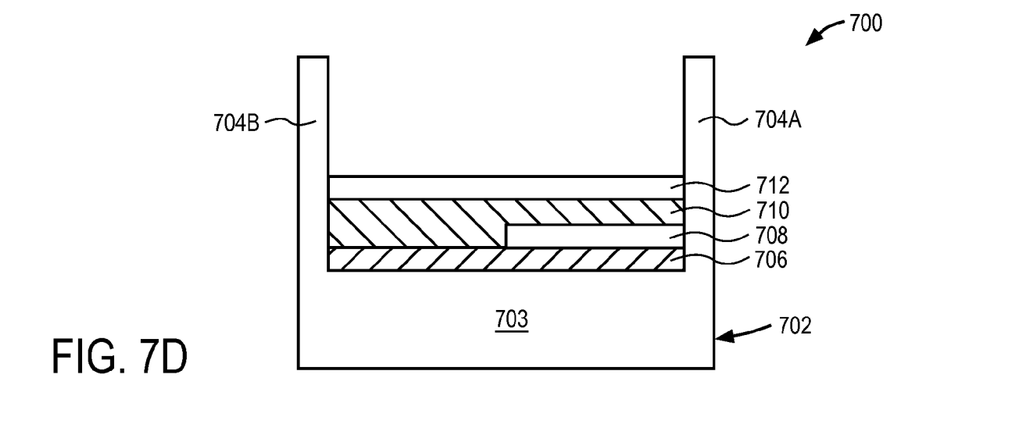
FIG. 7D illustrates one embodiment of another processing step for fabricating the optical microphone of FIG. 2A.

FIG. 7D illustrates one embodiment of another processing step for fabricating the optical microphone of FIG. 2A. FIG. 7D illustrates the step of forming a back plate layer 712 over sacrificial layer 710. Back plate layer 712 may be formed by any MEMS processing step suitable for forming a back plate layer over sacrificial layer 710. For example, back plate layer 712 may be formed by blanket depositing a back plate layer material over sacrificial layer 710 using CVD. A suitable back plate layer material may be, for example, a silicon material capable of forming a substantially rigid layer that can function as an electrode during operation of the microphone.

Figure 7E:
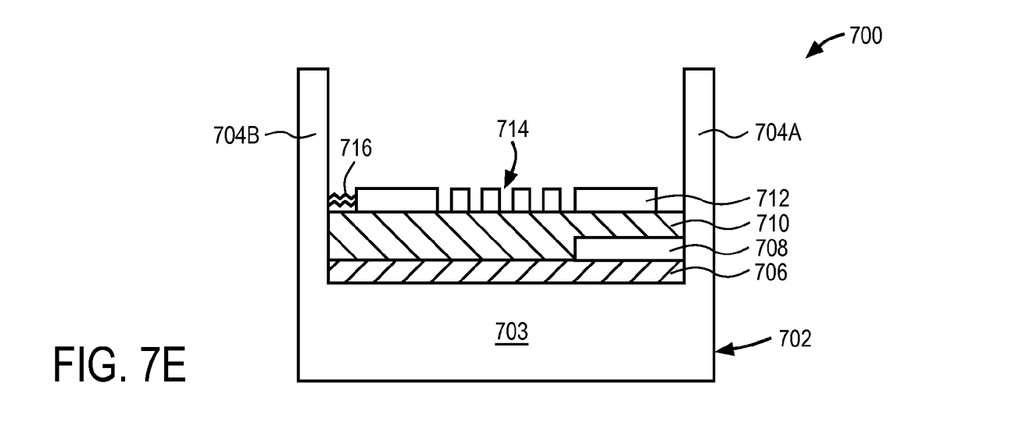
FIG. 7E illustrates one embodiment of another processing step for fabricating the optical microphone of FIG. 2A.

FIG. 7E illustrates one embodiment of another processing step for fabricating the optical microphone of FIG. 2A. FIG. 7E shows back plate layer 712 after a processing step in which portions of back plate layer 712 are removed to form a structure suitable for use as a back plate within microphone 200. For example, back plate layer 712 is processed using MEMS processing techniques to have the shape and dimensions of back plate 204 described in reference to FIG. 2A. Representatively, an RIE processing technique may be used to pattern back plate layer 712 such that it is separated from support member 704A and includes grating 714 and spring 716. Grating 714 and spring 716 may be substantially similar to grating 280 and spring 214 previously discussed in reference to FIG. 2A.

It should further be understood that since back plate layer 712 (e.g. back plate 204) is designed to be tilted onto base plate layer 708 (e.g. base plate 206) in the final product, a distance between back plate layer 712 and base plate layer 708, as well as a length of back plate layer 712, are selected to achieve the desired tilt angle. In other words, the tilt angle is controlled by the thickness of sacrificial layer 710 between base plate layer 708 and back plate layer 712. In this aspect, a thickness of sacrificial layer 710, is selected to achieve the desired tilt angle between the layers, for example, an acute tilt angle such as an angle of 4 degrees or less, for example, 3 degrees.

Figure 7F:
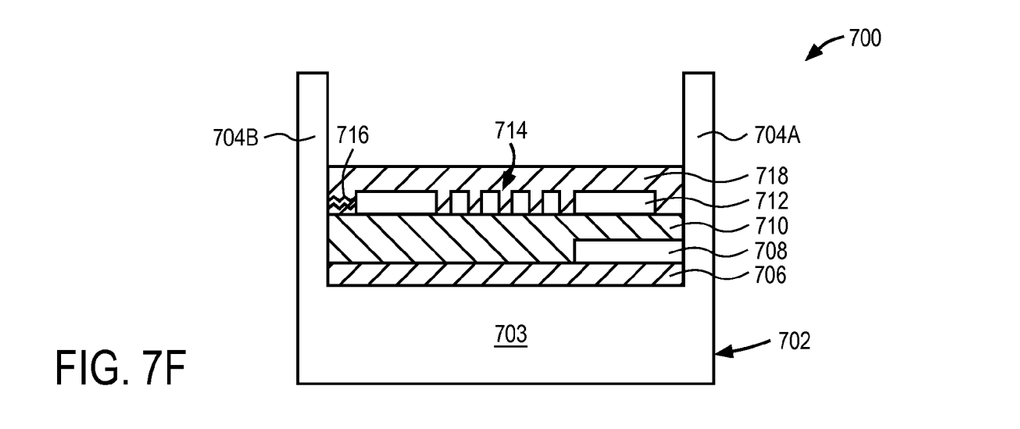
FIG. 7F illustrates one embodiment of another processing step for fabricating the optical microphone of FIG. 2A.

FIG. 7F illustrates one embodiment of another processing step for fabricating the optical microphone of FIG. 2A. FIG. 7F illustrates the step of forming a sacrificial layer 718 over back plate layer 712. Sacrificial layer 718 may be formed using any MEMS processing step suitable for forming a sacrificial layer over another layer. For example, sacrificial layer 718 may be formed by blanket depositing a sacrificial layer over back plate layer 712 and sacrificial layer 710 using CVD. Sacrificial layer 718 may be substantially similar to sacrificial layers 706 and 710. Sacrificial layer 718 may be of any material that can be selectively removed during a further processing step (e.g. silicon dioxide or silicate glass).

Figure 7G:
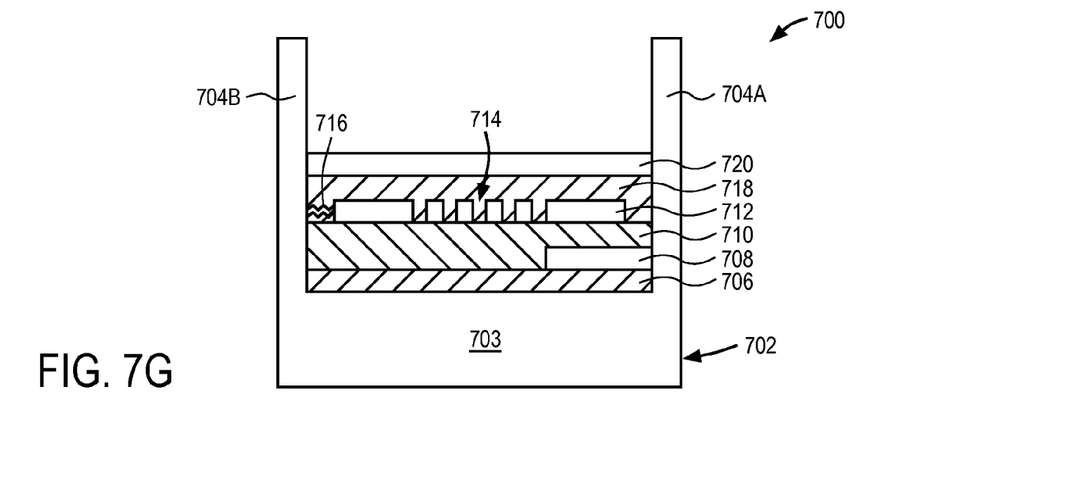
FIG. 7G illustrates one embodiment of another processing step for fabricating the optical microphone of FIG. 2A.

FIG. 7G illustrates one embodiment of another processing step for fabricating the optical microphone of FIG. 2A. FIG. 7G illustrates the step of forming a compliant membrane layer 720 over sacrificial layer 718. Compliant membrane layer 720 may be formed by any MEMS processing step suitable for forming a compliant membrane layer 720 over sacrificial layer 718. For example, compliant membrane layer 720 may be formed by blanket depositing a compliant membrane material over sacrificial layer 718 using CVD. A compliant membrane material may include, but is not limited to, a material capable of forming a membrane that can function as a microphone diaphragm and an electrode during a tilting operation of the microphone, for example, polysilicon or a metallic material.

Figure 7H:
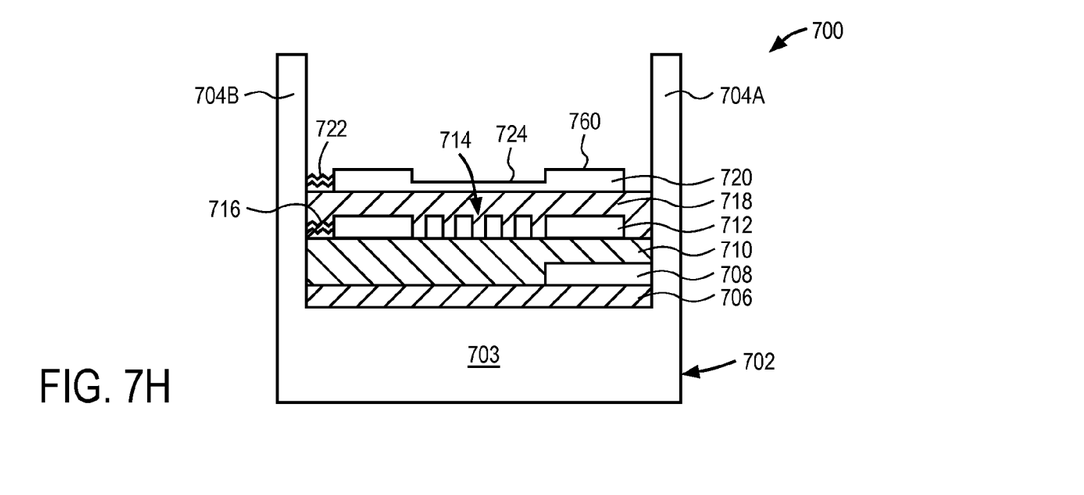
FIG. 7H illustrates one embodiment of another processing step for fabricating the optical microphone of FIG. 2A.

FIG. 7H illustrates one embodiment of another processing step for fabricating the optical microphone of FIG. 2A. FIG. 7H shows compliant membrane layer 720 after a processing step in which portions of compliant membrane layer 720 are patterned to form a structure suitable for use as a compliant membrane (e.g. a diaphragm) within microphone 200. For example, compliant membrane layer 720 is patterned using an RIE technique to have the shape and dimensions of compliant membrane 202 described in reference to FIG. 2A. Representatively, RIE may be used to separate compliant membrane layer 720 from support member 704A as well as to form a more compliant center portion 724 (a portion with reduced thickness), a more rigid frame 760 (a portion thicker than center portion 724) and spring 722. Center portion 724 and spring 722 may be substantially similar to center portion 270 and spring 212 previously discussed in reference to FIG. 2A and frame 760 may be substantially similar to frame 302 discussed in reference to FIG. 3.

Figure 7I:
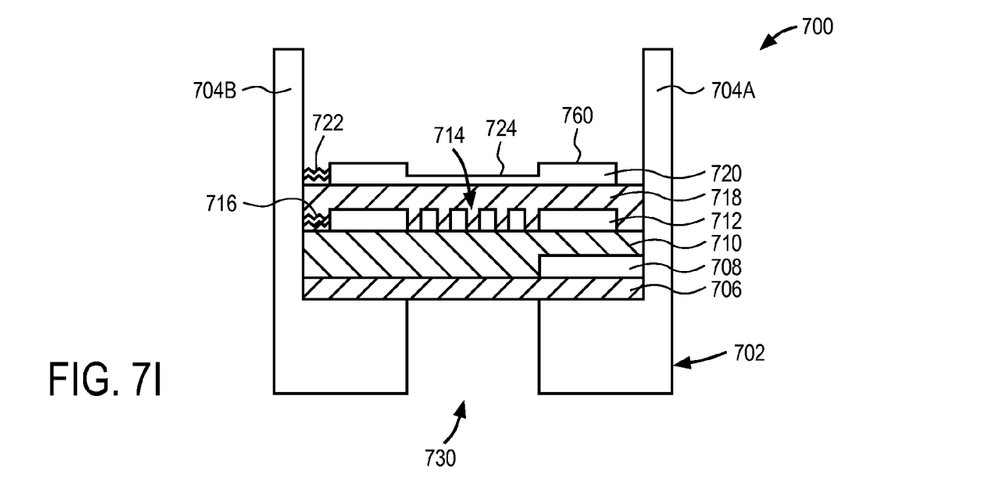
FIG. 7I illustrates one embodiment of another processing step for fabricating the optical microphone of FIG. 2A.

FIG. 7I illustrates one embodiment of another processing step for fabricating the optical microphone of FIG. 2A. FIG. 7I shows formation of an opening 730 within substrate 702. Opening 730 can be formed by any standard MEMS processing technique, for example, RIE or a deep reactive ion etching (DRIE) step. Opening 730 facilitates removal of sacrificial layers 706, 710 and 718.

Figure 7J:
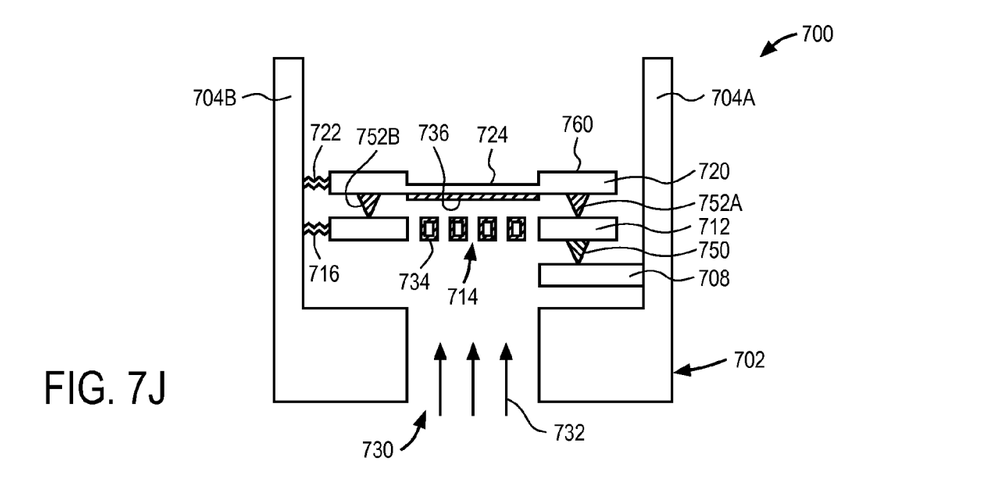
FIG. 7J illustrates one embodiment of another processing step for fabricating the optical microphone of FIG. 2A.

Representatively, FIG. 7J illustrates a processing step in which sacrificial layers 706, 710 and 718 have been removed, for example, by a wet or dry etch processing technique. For example, layers 706, 710 and 718 may be removed using a wet etching step with a selective wet etchant including hydrofluoric acid (HF). The wet etchant (HF) etches away sacrificial layers 706, 710 and 718 without etching, or otherwise damaging, the various layers needed to form the microphone, for example, base plate layer 708, back plate layer 712 and compliant membrane layer 720. In some embodiments, portions of sacrificial layers 718 and 710 may be patterned and not completely removed such that spacers 750, 752A and 752B, which, for example, correspond to spacers 236, 216A and 216B remain between the layers.

FIG. 7J further illustrates the step of applying a reflective surface 736 to center portion 718 and a reflective surface 734 to grating 714. Representatively, in one embodiment, reflective surface 736 and reflective surface 734 are formed by introducing a reflective material 732 (e.g. gold coating) through opening 730 within substrate in a manner that allows material 732 to coat center portion 718 and grating 714.

Once each of the layers necessary for operation of microphone 700 are formed, an emitter (e.g. emitter 260) and detector (e.g. detector 262) can be positioned within opening 730 such that they are aligned with grating 714 and reflective surface 736. In one embodiment, emitter and detector may be formed monolithically on another substrate using standard MEMS processing techniques, and then positioned within, or aligned with, opening 730. Microphone 700 may then be mounted within an enclosure (e.g. enclosure 240) which can in turn be mounted within the desired electronic device. Alternatively, the emitter and detector may be mounted within an enclosure for the microphone and positioned within opening 730. In addition, any circuitry (e.g. wires) connected to the various microphone components, for example, base layer 708, back plate layer 712, compliant membrane layer 720, the emitter or the detector may be pre-formed within substrate 702 and support members 704A-704B such that when the components are formed, the circuitry is connected to the components.

Figure 8:
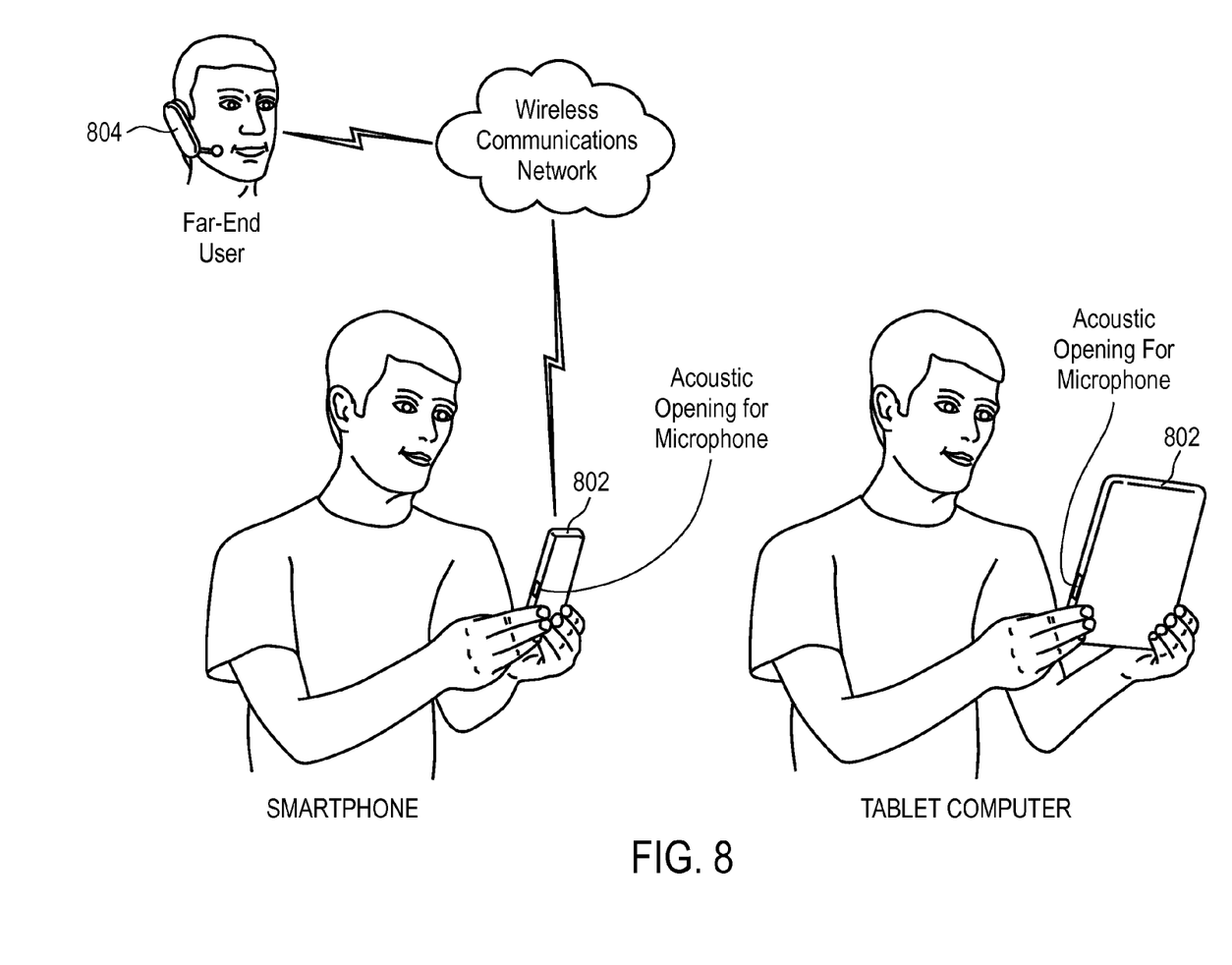
FIG. 8 illustrates one embodiment of a simplified schematic view of one embodiment of an electronic device in which the optical microphone may be implemented.

FIG. 8 illustrates one embodiment of a simplified schematic view of one embodiment of an electronic device in which a MEMS optical microphone, or other MEMS device described herein, may be implemented. As seen in FIG. 8, the MEMS device may be integrated within a consumer electronic device 802 such as a smart phone with which a user can conduct a call with a far-end user of a communications device 804 over a wireless communications network; in another example, the MEMS device may be integrated within the housing of a tablet computer. These are just two examples of where the MEMS device described herein may be used, it is contemplated, however, that the MEMS device may be used with any type of electronic device in which a MEMS device, for example, an optical MEMS microphone, is desired, for example, a tablet computer, a desk top computing device or other display device.

Figure 9:
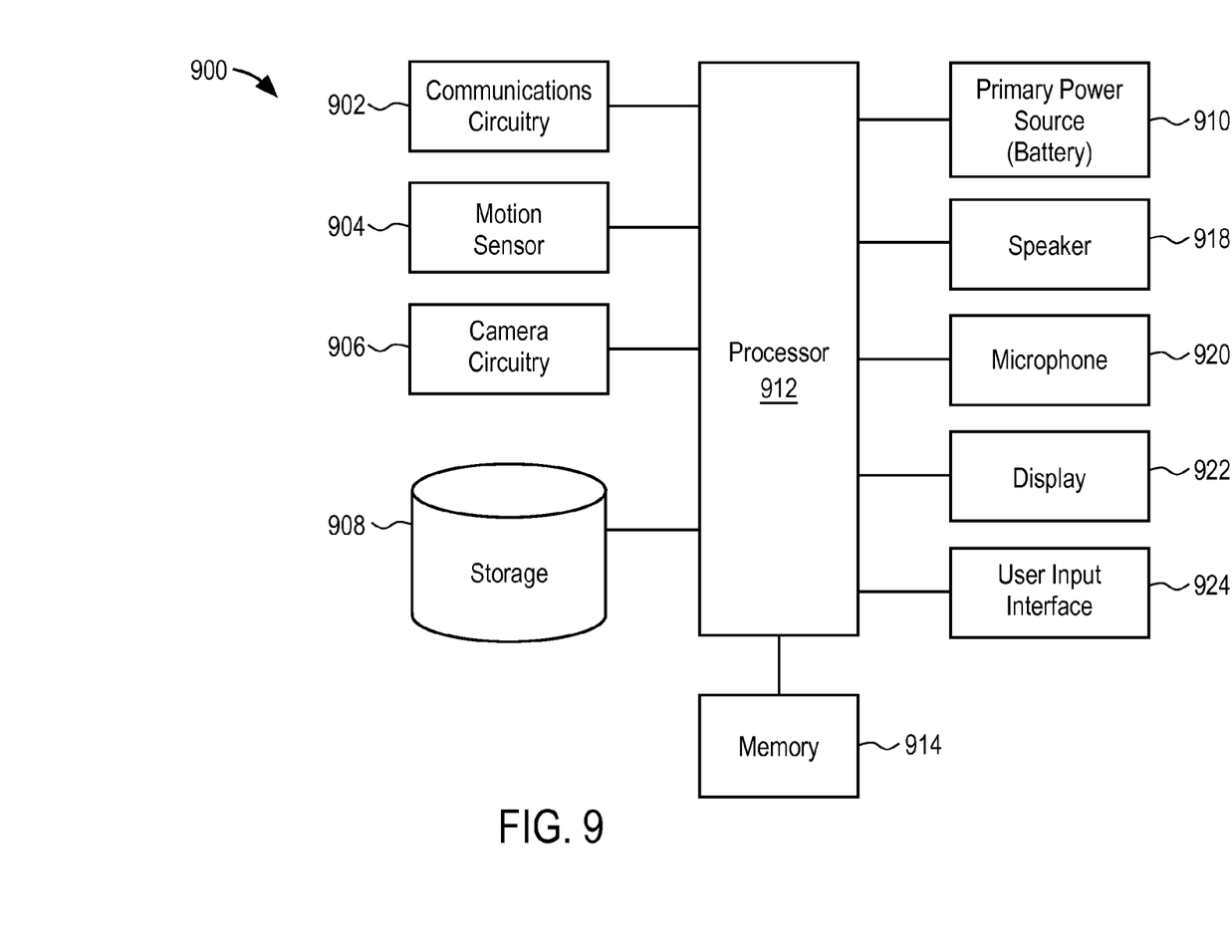
FIG. 9 illustrates a block diagram of some of the constituent components of an embodiment of an electronic device in which an embodiment of the invention may be implemented.

FIG. 9 illustrates a block diagram of some of the constituent components of an embodiment of an electronic device in which an embodiment of the invention may be implemented. Device 900 may be any one of several different types of consumer electronic devices. For example, the device 900 may be any microphone-equipped mobile device, such as a cellular phone, a smart phone, a media player, or a tablet-like portable computer.

In this aspect, electronic device 900 includes a processor 912 that interacts with camera circuitry 906, motion sensor 904, storage 908, memory 914, display 922, and user input interface 924. Main processor 912 may also interact with communications circuitry 902, primary power source 910, speaker 918, and microphone 920. The various components of the electronic device 900 may be digitally interconnected and used or managed by a software stack being executed by the processor 912. Many of the components shown or described here may be implemented as one or more dedicated hardware units and/or a programmed processor (software being executed by a processor, e.g., the processor 912).

The processor 912 controls the overall operation of the device 900 by performing some or all of the operations of one or more applications or operating system programs implemented on the device 900, by executing instructions for it (software code and data) that may be found in the storage 908. The processor 912 may, for example, drive the display 922 and receive user inputs through the user input interface 924 (which may be integrated with the display 922 as part of a single, touch sensitive display panel). In addition, processor 912 may send an audio signal to speaker 918 to facilitate operation of speaker 918.

Storage 908 provides a relatively large amount of "permanent" data storage, using nonvolatile solid state memory (e.g., flash storage) and/or a kinetic nonvolatile storage device (e.g., rotating magnetic disk drive). Storage 908 may include both local storage and storage space on a remote server. Storage 908 may store data as well as software components that control and manage, at a higher level, the different functions of the device 900.

In addition to storage 908, there may be memory 914, also referred to as main memory or program memory, which provides relatively fast access to stored code and data that is being executed by the processor 912. Memory 914 may include solid state random access memory (RAM), e.g., static RAM or dynamic RAM. There may be one or more processors, e.g., processor 912, that run or execute various software programs, modules, or sets of instructions (e.g., applications) that, while stored permanently in the storage 908, have been transferred to the memory 914 for execution, to perform the various functions described above.

The device 900 may include communications circuitry 902. Communications circuitry 902 may include components used for wired or wireless communications, such as two-way conversations and data transfers. For example, communications circuitry 902 may include RF communications circuitry that is coupled to an antenna, so that the user of the device 900 can place or receive a call through a wireless communications network. The RF communications circuitry may include a RF transceiver and a cellular baseband processor to enable the call through a cellular network. For example, communications circuitry 902 may include Wi-Fi communications circuitry so that the user of the device 900 may place or initiate a call using voice over Internet Protocol (VOIP) connection, transfer data through a wireless local area network.

The device may include a microphone 920. Microphone 920 may be a MEMS optical microphone such as that described in reference to FIG. 2A-2B. In this aspect, microphone 920 may be an acoustic-to-electric transducer or sensor that converts sound in air into an electrical signal. The microphone circuitry (e.g. circuit 224) may be electrically connected to processor 912 and power source 910 to facilitate the microphone operation (e.g. tilting).

The device 900 may include a motion sensor 904, also referred to as an inertial sensor, that may be used to detect movement of the device 900. Motion sensor 904 could, in some embodiments, include MEMS device FIG. 1A-FIG. 1B. The motion sensor 904 may include a position, orientation, or movement (POM) sensor, such as an accelerometer, a gyroscope, a light sensor, an infrared (IR) sensor, a proximity sensor, a capacitive proximity sensor, an acoustic sensor, a sonic or sonar sensor, a radar sensor, an image sensor, a video sensor, a global positioning (GPS) detector, an RF or acoustic doppler detector, a compass, a magnetometer, or other like sensor. For example, the motion sensor 904 may be a light sensor that detects movement or absence of movement of the device 900, by detecting the intensity of ambient light or a sudden change in the intensity of ambient light. The motion sensor 904 generates a signal based on at least one of a position, orientation, and movement of the device 900. The signal may include the character of the motion, such as acceleration, velocity, direction, directional change, duration, amplitude, frequency, or any other characterization of movement. The processor 912 receives the sensor signal and controls one or more operations of the device 900 based in part on the sensor signal.

The device 900 also includes camera circuitry 906 that implements the digital camera functionality of the device 900. One or more solid state image sensors are built into the device 900, and each may be located at a focal plane of an optical system that includes a respective lens. An optical image of a scene within the camera's field of view is formed on the image sensor, and the sensor responds by capturing the scene in the form of a digital image or picture consisting of pixels that may then be stored in storage 908. The camera circuitry 906 may also be used to capture video images of a scene.

Device 900 also includes primary power source 910, such as a built in battery, as a primary power supply.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, the devices and processing steps disclosed herein may correspond to any type of MEMS sensor that can benefit from being able to tilt one or more plates or layers within the sensor, for example, an inertial sensor, an accelerometer, a gyrometer or the like. Still further, in some embodiments, the MEMS sensor includes only two plates, and only one of the plates is movable. For example, the MEMS sensor may include a top plate having a sensor surface, a base plate and circuitry to apply a voltage between the two plates. The voltage causes only one of the plates to move with respect to the other plate (e.g. the movable plate can be the top plate with the sensor, which could be a sound pick up membrane). The description is thus to be regarded as illustrative instead of limiting.

What is claimed is:

1. A micro-electro-mechanical system (MEMS) optical sensor comprising:
   a substrate having a base portion and a vertically extending support portion;
   a top plate having a compliant membrane configured to vibrate in response to acoustic waves, the top plate connected to the support portion so as to tilt, the compliant membrane having a reflective surface portion;
   a back plate connected to the support portion so as to tilt, and being spaced apart from the compliant membrane, the back plate having a grating portion positioned below the reflective surface portion;
   a base plate connected to the support portion at a position below the back plate;
   a light emitter positioned on the base portion below the back plate and configured to transmit a laser light through the grating portion and toward the reflective surface portion of the compliant membrane;
   a light detector positioned on the base portion below the back plate and configured to detect a diffracted pattern of the laser light after reflection from the reflective surface; and
   circuitry operable to apply a voltage to one or more of the back plate and the top plate, relative to the base plate, that causes tilting of the top plate and the back plate with respect to the base plate.

2. The optical sensor of claim 1 wherein the compliant membrane is a MEMS microphone diaphragm.

3. The optical sensor of claim 1 wherein the MEMS optical sensor is an optical microphone.

4. The optical sensor of claim 1 wherein each of the top plate and the back plate comprise a first end movably connected to the support portion and a second free end.

5. The optical sensor of claim 1 wherein tilting the top plate and the back plate with respect to the base plate comprises moving the top plate and the back plate while the base plate remains stationary.

6. The optical sensor of claim 1 wherein the tilt of the top plate and the back plate with respect to the base plate is at an acute angle.

7. The optical sensor of claim 1 wherein each of the top plate and the back plate are connected to the vertically extending support portion by a spring.

8. The optical sensor of claim 1 wherein the top plate comprises a frame and spokes for suspending the compliant membrane within the frame.

9. The optical sensor of claim 1 wherein posts are positioned between the top plate and the back plate to define a controlled minimal stress region of operation for the top plate.

10. The optical sensor of claim 1 wherein the top plate and the back plate are tilted toward the base plate.

11. The optical sensor of claim 1 wherein application of a current by the circuitry produces an electrostatic force operable to draw the back plate and the top plate toward the base plate.

* * * * *